(12) United States Patent
Christopher et al.

(10) Patent No.: US 11,298,232 B2
(45) Date of Patent: Apr. 12, 2022

(54) CRANIAL IMPLANT WITH DURAL WINDOW

(71) Applicant: Longeviti Neuro Solutions LLC, Hunt Valley, MD (US)

(72) Inventors: Jesse Christopher, Hunt Valley, MD (US); Bradley Rabinovitz, Annapolis, MD (US); Chad R. Gordon, Cockeysville, MD (US)

(73) Assignee: LONGEVITI NEURO SOLUTIONS LLC, Hunt Valley, MD (US)

( * ) Notice: Subject to any disclaimer, the term of this patent is extended or adjusted under 35 U.S.C. 154(b) by 56 days.

(21) Appl. No.: 16/721,392

(22) Filed: Dec. 19, 2019

(65) Prior Publication Data
US 2020/0197180 A1 Jun. 25, 2020

Related U.S. Application Data

(60) Provisional application No. 62/781,925, filed on Dec. 19, 2018.

(51) Int. Cl.
| | | |
|---|---|---|
| *A61B 5/00* | (2006.01) | |
| *A61F 2/28* | (2006.01) | |
| *A61F 2/30* | (2006.01) | |

(52) U.S. Cl.
CPC .......... *A61F 2/2875* (2013.01); *A61B 5/0059* (2013.01); *A61B 5/4064* (2013.01); *A61F 2/30749* (2013.01); *A61F 2002/3008* (2013.01); *A61F 2002/3009* (2013.01); *A61F 2002/30092* (2013.01); *A61F 2310/00353* (2013.01)

(58) Field of Classification Search
CPC ............................................... A61B 2090/103
See application file for complete search history.

(56) References Cited

U.S. PATENT DOCUMENTS

| | | | | |
|---|---|---|---|---|
| 4,981,142 A | * | 1/1991 | Dachman | A61B 6/0414 128/897 |
| 5,397,361 A | * | 3/1995 | Clark | C08L 33/04 128/898 |
| 5,861,034 A | * | 1/1999 | Taira | A61L 27/48 623/11.11 |
| 5,902,326 A | | 5/1999 | Lessar et al. | |

(Continued)

FOREIGN PATENT DOCUMENTS

WO 1998041152 A1 9/1998

OTHER PUBLICATIONS

Shaunacy Ferro, Clear Cranial Implant Lets Doctors See Into the Brain, https://www.popsci.com/science/article/2013-09/clear-cranial-implant-lets-doctors-see-brain/, Sep. 4, 2013.

(Continued)

*Primary Examiner* — Jacqueline Woznicki
(74) *Attorney, Agent, or Firm* — Welsh Flaxman & Gitler LLC (57) ABSTRACT

A cranial implant for access to a cerebral cortex includes a window member shaped and dimensioned for positioning within a dural defect to provide access through the dura such that access to the cerebral cortex is provided in a location under study. An implant body is provided having a geometry that substantially conforms to a resected portion of a patient's anatomy to which the implant body is to be secured.

10 Claims, 9 Drawing Sheets

(56) References Cited

U.S. PATENT DOCUMENTS

| | | | |
|---|---|---|---|
| 6,004,328 A * | 12/1999 | Solar | A61M 25/0119 |
| | | | 623/1.11 |
| 6,267,772 B1 | 7/2001 | Mulhauser et al. | |
| 7,717,853 B2 | 5/2010 | Nita | |
| 8,116,875 B2 | 2/2012 | Osypka et al. | |
| 8,306,607 B1 | 11/2012 | Levi et al. | |
| 8,840,556 B2 | 9/2014 | Lin et al. | |
| 9,044,195 B2 | 6/2015 | Manwaring et al. | |
| 9,179,850 B2 | 11/2015 | Wingeier et al. | |
| 9,440,064 B2 | 9/2016 | Wingeier et al. | |
| 9,462,958 B2 | 10/2016 | Osorio et al. | |
| 9,535,192 B2 | 1/2017 | Aguilar-Mendoza et al. | |
| 9,592,124 B2 * | 3/2017 | Joganic | A61F 2/50 |
| 9,993,337 B1 * | 6/2018 | Brogan | A61F 2/2875 |
| 10,966,833 B2 * | 4/2021 | Sampath | A61D 7/00 |
| 2002/0198559 A1 * | 12/2002 | Mistry | A61M 25/10 |
| | | | 606/194 |
| 2004/0073270 A1 | 4/2004 | Firlik et al. | |
| 2004/0243145 A1 * | 12/2004 | Bobo, Sr. | A61B 5/031 |
| | | | 606/129 |
| 2005/0008660 A1 | 1/2005 | Kipke et al. | |
| 2006/0224242 A1 * | 10/2006 | Swords | A61B 17/8085 |
| | | | 623/17.19 |
| 2007/0038100 A1 | 2/2007 | Nita | |
| 2007/0129652 A1 * | 6/2007 | Nita | A61M 37/0092 |
| | | | 601/2 |
| 2009/0254052 A1 | 10/2009 | Birk et al. | |
| 2010/0211026 A2 * | 8/2010 | Sheetz | A61M 39/0247 |
| | | | 604/288.02 |
| 2011/0270373 A1 * | 11/2011 | Sampognaro | A61F 2/844 |
| | | | 623/1.11 |
| 2012/0259428 A1 * | 10/2012 | Brogan | A61F 2/0059 |
| | | | 623/23.72 |
| 2013/0304216 A1 * | 11/2013 | Paspa | A61F 2/2875 |
| | | | 623/17.19 |
| 2014/0074202 A1 * | 3/2014 | Bedenbaugh | A61N 1/0539 |
| | | | 607/116 |
| 2014/0172014 A1 * | 6/2014 | Fitzgerald | A61F 2/2875 |
| | | | 606/213 |
| 2014/0309744 A1 * | 10/2014 | Batty | A61F 2/2875 |
| | | | 623/17.19 |
| 2014/0330123 A1 * | 11/2014 | Manwaring | A61B 8/4209 |
| | | | 600/438 |
| 2016/0184100 A1 | 6/2016 | Joganic | |
| 2016/0185046 A1 | 6/2016 | Littlefield | |
| 2016/0193048 A1 * | 7/2016 | Prada | A61F 2/2875 |
| | | | 623/17.19 |
| 2016/0296312 A1 | 10/2016 | Kuhn et al. | |
| 2017/0027629 A1 | 2/2017 | Ackerman et al. | |
| 2017/0156596 A1 | 6/2017 | Aguilar-Mendoza et al. | |
| 2017/0325961 A1 * | 11/2017 | Taira | C03C 10/16 |
| 2018/0055640 A1 * | 3/2018 | Gordon | B33Y 80/00 |
| 2018/0325672 A1 * | 11/2018 | Gordon | A61F 2/2875 |
| 2019/0192298 A1 * | 6/2019 | Gordon | A61F 2/2875 |
| 2019/0209328 A1 * | 7/2019 | Christopher | A61N 1/37518 |
| 2019/0239868 A1 * | 8/2019 | Attenborough | A61F 2/30942 |
| 2020/0030099 A1 * | 1/2020 | Sampath | A61B 8/4416 |
| 2020/0030103 A1 * | 1/2020 | Di Meco | A61F 2/30942 |
| 2020/0138580 A1 * | 5/2020 | Carpentier | A61F 2/2875 |
| 2020/0375745 A1 * | 12/2020 | Sampath | A61N 1/37514 |

OTHER PUBLICATIONS

J. Tobias et al., An ultrasound window to perform scanned, focused ultrasound hyperthermia treatments of brain tumors, Am. Assoc Phys. Med , Mar.-Apr. 1987;14(2):228-34.

John Hewitt, Transparent skull implant for easier, cheaper laser-based brain scanning, https://www.extremetech.com/extreme/165571-transparent-skull-implant-for-easier-cheaper-laser-based-brain-scanning, Sep. 5, 2013.

* cited by examiner

CRANIAL IMPLANT WITH DURAL WINDOW

CROSS REFERENCE TO RELATED APPLICATION

This application claims the benefit of U.S. Provisional Patent Application Ser. No. 62/781,925, entitled "CRANIAL IMPLANT WITH DURAL WINDOW," filed Dec. 19, 2018, the content of which is incorporated herein by reference.

BACKGROUND OF THE INVENTION

1. Field of the Invention

The invention relates to a cranial implant, and associated methods, allowing for clear and unobstructed visualization or imaging of the brain, as well as replacement or substitution of excised dura with or without simultaneous skull reconstruction.

2. Description of the Related Art

The brain is surrounded by three layers of membrane called meninges. The meninges are positioned between the cerebral cortex and the cranium. The outermost of the meninges is the dura, the innermost of the meninges is the pia mater, and the arachnoid mater is the middle meningeal membrane that is positioned between the dura and the pia mater. The dura is a thick membrane and often impedes the visual or optical access to the cerebral cortex. In fact, when a resected portion of the skull is removed during a cranial procedure, the meninges, in particular, the dura, prevent the surgeon from clearly viewing the cerebral cortex.

With this in mind, a need exists for methods and apparatuses to balance the need for optically and visually accessing the brain with the need to protect the brain.

SUMMARY

According to a first aspect there may be provided a cranial implant for access to a cerebral cortex. The cranial implant includes a window member shaped and dimensioned for positioning within a dural defect to provide access through the dura such that access to the cerebral cortex is provided in a location under study. The cranial implant also includes an implant body having a geometry that substantially conforms to a resected portion of a patient's anatomy to which the implant body is to be secured.

In some embodiments the window member may sonolucent allowing for passage of ultrasonic waves therethrough.

In some embodiments the window member may be optically clear in the visible light spectrum allowing for optical and/or visual access therethough.

In some embodiments the implant body may include at least one implant body etching providing for a location identifying image. In another embodiment the window member may include a window etching that merges with the at least one implant body etching to define a single location identifying image. In a further embodiment the at least one implant body etching and the window etching may include radiographic materials.

In accordance with yet another embodiment the implant body may include an outer first implant body etching and an inner second implant body etching respectively formed along outer and inner surfaces of the implant body. The outer first implant body etching and the inner second implant body etching may merge to define a single location identifying image. The outer first implant body etching and the inner second implant body etching may include radiographic materials.

In some embodiments the implant body may be made of clear PMMA.

In some embodiments the window member and the implant body may be integrally formed. In an embodiment, the window member may have a diameter of approximately 5 mm to 45 mm.

In accordance with another embodiment, the cranial implant may further include a coupling ring securing the window member within an opening formed within the dura. The coupling ring may be made of a shape memory ring.

In another embodiment, the window member and the implant body may be separate and distinct elements. The window member may be selectively secured to an underside of the implant body.

In a further aspect there may be provided a cranial implant for access to a cerebral cortex wherein a window member shaped and dimensioned for positioning within a dura is provided. The window member is adapted for use in conjunction with a cranial implant body in a manner providing access through the dura and to the cerebral cortex in a location under study. The window member may be sonolucent allowing for passage of ultrasonic waves therethrough. The window member may be optically clear in the visible light spectrum allowing for optical and/or visual access therethough.

In yet another aspect a method for providing access to a cerebral cortex is disclosed. The method includes forming an opening defining a dural defect in a dura of a patient, securing a window member within the dural defect, wherein the window member provides access to the cerebral cortex in a location under study, and securing an implant body over the window member.

Additional advantages of the embodiments will be set forth in part in the description which follows, and in part will be understood from the description, or may be learned by practice of the invention. The advantages will be realized and attained by means of the elements and combinations particularly pointed out in the appended claims.

DETAILED DESCRIPTION

The descriptions of the various embodiments of the present invention are presented with reference to the accompanying drawings for purposes of illustration, but are not intended to be exhaustive or limited to the embodiments disclosed. Many modifications and variations will be apparent to those of ordinary skill in the art without departing from the scope and spirit of the described embodiments. The various embodiments are not necessarily mutually exclusive, as some embodiments can be combined with one or more other embodiments to form new embodiments. Therefore, the details disclosed herein are not to be interpreted as limiting, but merely as a basis for teaching one skilled in the art how to make and/or use the various embodiments.

The present reconstructive cranial implant is directed to the provision of a dural window for visual and/or optical access to the cerebral cortex 18. As will be appreciated based upon the following disclosure, in addition to providing visual and/or optical access to the cerebral cortex, the provision of a dural window also provides for access to the brain via ultrasound and radiation for various diagnostic, therapeutic, and imaging purposes. As will be appreciated based upon the following disclosure, and considering the fact the cranial implant of the disclosed embodiment is considered to include a window member that is positioned within a dural defect created in the dura for the placement of the window member therein, so as to define a dural window, the term cranial implant is broadly used herein as referring to implants intended for placement within the cranium and dura of a patient, which might otherwise be referred to as cranial-dural implants. With reference to FIGS. 1 to 6, a reconstructive cranial implant (or other reconstructive cranial device) 110, 210 incorporating a window member 130, 230 is disclosed. As will be appreciated based upon the following disclosure, the window member 130, 230 provides a clear view through the dura 12 such that visual and/or optical access to the cerebral cortex 18 is fully provided in the location under study. The provision of visual and/or optical access is intended to cover both viewing by a surgeon or other medical practitioner, as well as the passage of both visible and non-visible (for example, ultraviolet, infrared, etc.) light (that would otherwise be blocked by the dura) therethrough for the purpose of imaging, therapy, and other medically beneficial application. Further still, and as will be appreciated based upon the following disclosure, the optical clarity of the dural window member 130, 230 in the visible light spectrum allows for observation of a diagnostic marker(s) in/on the brain, such as, a thermometer, pressure sensor, etc. If the window member is flexible enough, it may be used for dural replacement as well.

As those skilled in the art will appreciate, and as briefly mentioned above, the brain 10 is surrounded by three layers of membrane called meninges 12, 14, 16. The meninges 12, 14, 16 are, therefore, positioned between the cerebral cortex 18 and the endocranium 20, that is, the inner surface of the cranium. The outermost of the meninges is the dura 12. The dura 12 is a thick membrane that surrounds the brain 10 and is positioned adjacent the endocranium 20. The innermost of the meninges is the pia mater 14. The pia mater 14 is a delicate membrane directly covering the cerebral cortex 18. Finally, the arachnoid mater 16 is the middle meningeal membrane and is positioned between the dura 12 and the pia mater 14. The arachnoid mater 16 is a delicate membrane attached to the inside of the dura 12. It is appreciated that the following disclosure relates to a cranial implant 10 adapted for adult patients. As such, and considering the fact the dura 12 is much thinner in pediatric neurosurgery patients and/or in patients who have received radiation therapy for neuro-oncological disease, the reconstructive cranial implant 110, 210 may be slightly modified to suit these anatomical variables.

When the resected portion of the skull 24 is removed during a cranial procedure, the meninges 12, 14, 16, in particular, the dura 12, prevent the surgeon from clearly viewing the cerebral cortex 18. It is important that the meninges 12, 14, 16 remain intact to prevent leakage of cerebrospinal fluid (CSF), protect the brain 10 from damaging contact, protect the brain 10 from infection, and protect the brain 10 from other undesirable access. With this in mind, and in an effort to balance the need for viewing of the cerebral cortex 18 with the need to protect the brain within a water-tight environment, the reconstructive cranial implant 110, 210 is provided with a window member 130, 230 for positioning within a dural defect created in the dura 12 for the placement of the window member 130, 230 so that a clear view of the cerebral cortex 18 is provided in the location under study allowing for visual and/or optical access. However, the window member 130, 230 is structured such that it maintains the continuous surface of the meninges 12, 14, 16 and as such minimizes the negative effects that might result if one were to maintain the dura 12 open for an extended period of time (i.e. CSF leak).

The reconstructive cranial implant 110, 210 includes an implant body 112, 212 structured in a manner as used and known by those skilled in the art of cranial surgical procedures. The implant body 112, 212 may take a variety of forms and are most commonly shaped and dimensioned for integration into the structure of a patient's skull; that is, the implant body 112, 212 has a geometry that substantially conforms to a resected portion of the patient's anatomy to which the implant is to be secured. Briefly, the implant body 112, 212 includes an outer (commonly convex) first surface 112o, 212o an inner (commonly concave) second surface 112i, 212i, and a peripheral edge 112p, 212p extending between the outer first surface 112o, 212o and the inner second surface 112i, 212i. The implant body 112, 212 is shaped and dimensioned for engagement with the skull of the patient upon implantation in a manner well known to those skilled in the field of neurosurgical and neuroplastic reconstructive procedures. The outer first surface 112o, 212o and inner second surface 112, 212 of the implant body 112, 212 are preferably curved in a superior to inferior direction, a posterior to anterior direction, and a medial to lateral direction. In addition, the peripheral edge 112p, 212p has a substantial taper for resting upon a matching taper formed along the skull. It is, however, appreciated that this taper may vary (or not exist at all, that is, the peripheral edge 112p, 212p may be substantially perpendicular relative to the outer first surface 112o, 212o and the inner second surface 112i, 212i) depending upon the specific needs of the procedure.

In accordance with an embodiment, the implant body 112, 212 is fabricated from a wide array of commonly-available biomaterials including, but not limited to, clear and/or opaque PMMA (Poly(methyl methacrylate)), PEEK (Polyether ether ketone), PEKK (Polyetherketoneketone), porous polyethylene, flexible silicone, cubic zirconium, titanium alloy, allograft, autograft, xenograft, glass, and/or various other tissue-engineered constructs. In fact, some of the biomaterials used in this novel device may be resorbable versus permanent with respect to time. Also, the device may have a varying amount of biomaterials given that the dural replacement requires flexibility properties and the cerebrocranial protection property requires a stiff material. In accordance with one embodiment, the implant body 112, 212 is ideally made of clear PMMA since it's fully translucent to light, sonolucent to ultrasound such that it allows for the passage of ultrasonic waves without the production of echoes that are due to reflection (as first described by Gordon et al. in "Sonolucent Cranial Implants: Cadaveric study and Clinical Findings Supporting Diagnostic and Therapeutic Trans-Cranioplasty Ultrasound. J Craniofac Surg 2019 and Gordon et al. in "Trans-Cranioplasty Ultrasound (TCU) through a Sonolucent Cranial Implant Made of Poly-methyl methacrylate (PMMA): Phantom Study Comparing Ultrasound, CT and MRI. J Craniofac Surg 2019), permeable to low-coherence light used in optical coherence tomography (OCT), radiolucent such that it is permeable to various forms of electromagnetic radiation (for example, is permeable to ECoG (electrocorticographic) signals), and transparent for ideal visualization necessary for brain lead placement, catheter positioning, etc. This allows for the critical transmission of vital imaging with minimal distortion, such as direct visual inspection of the brain, ultrasound waves for brain pathology detection, low-coherence light used in optical coherence tomography (OCT), and wireless signal communication (i.e., electroencephalography or ECoG)—essential for various neuromodulation devices such as NeuroPace®, for example. Another clear material that may be readily used in accordance with the present reconstructive cranial implant is cubic zirconium or plastic.

The optical clarity of the implant body 112, 212 is important in that it provides for the provision of high optical clarity allowing for optical links connecting the external environment to the surface of the brain (for example, transmitting between the cortex and the other side of the reconstructive cranial implant 110, 210). Visualization devices such as high-definition cameras, ultrasound probes, or optical coherence tomography (OCT) imaging devices may therefore be used in conjunction with the reconstructive cranial implant.

Still further, the implant body 112, 212 is constructed of a material allowing for imaging of the brain through the reconstructive cranial implant 110, 210, for example, via ultra-sound or optical coherence tomography. It is known that clear PMMA will provide the ability to permit ultrasound imaging of the brain therethrough so long as it is manufactured without additives that might function to block the radio waves of the imaging device.

Figures 1, 2:
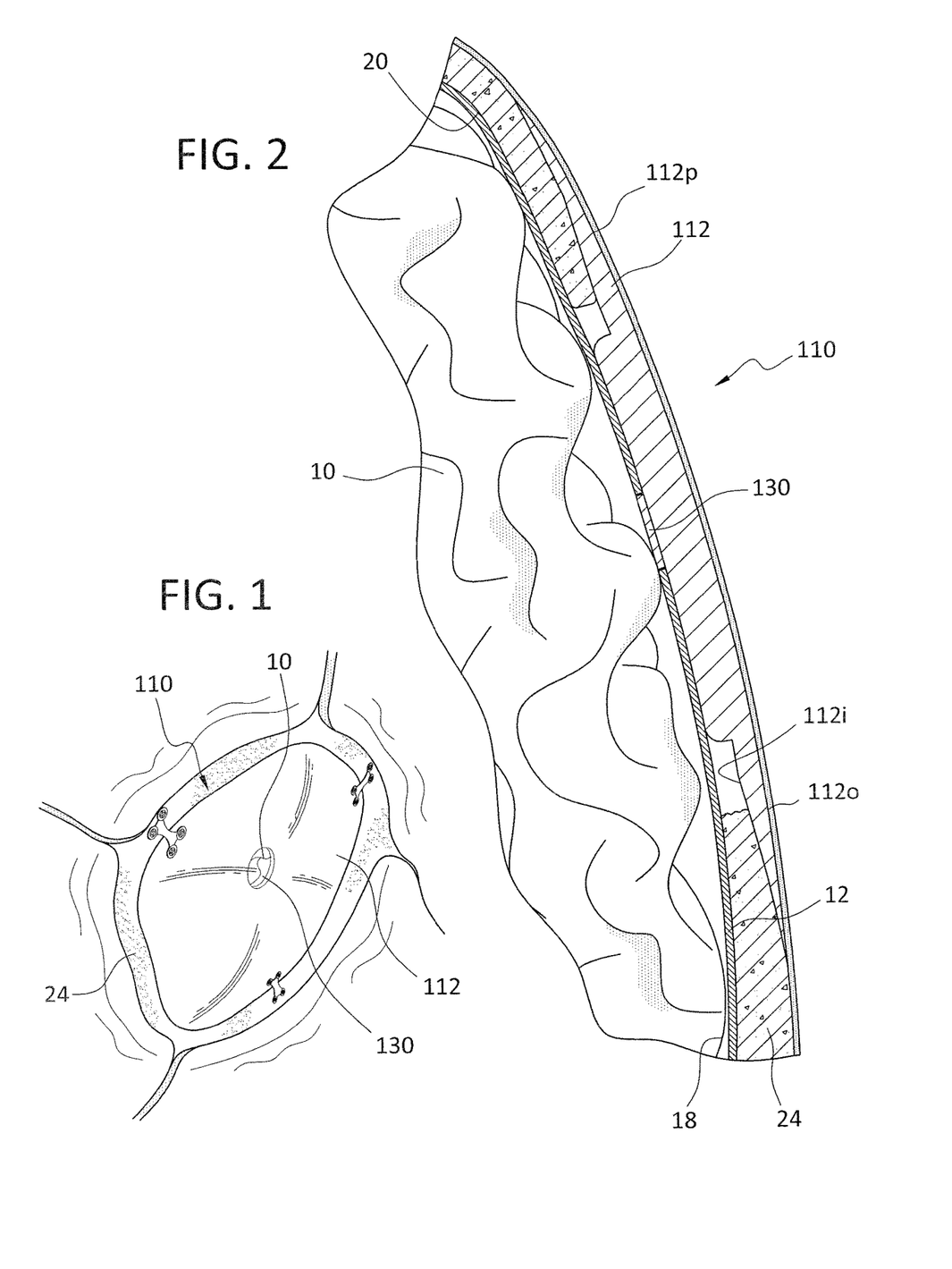
FIG. 1 is a perspective view of an installed cranial implant in accordance with a first embodiment.
FIG. 2 is a cross sectional view of the installed cranial implant shown in FIG. 1.
Figure 3:
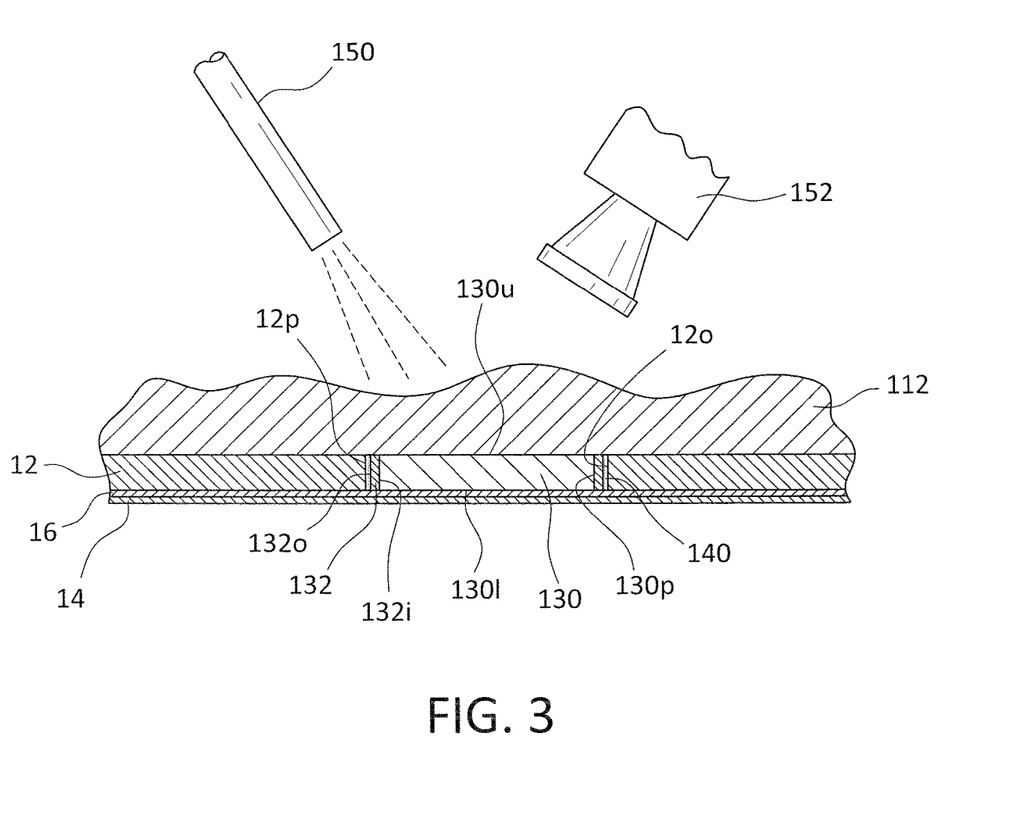
FIG. 3 is a detailed cross sectional view of the installed cranial implant shown in FIG. 1. It should be appreciated the surfaces of the dural window member and the implant body are shown as being substantially flat although it is appreciated these surfaces may be contoured as dictated by specific anatomical features and optical characteristics of the cranial implant.

In accordance with the embodiment disclosed with reference to FIGS. 1 to 3, the window member 130 is formed as an integral part of the implant body 112, and the window member 130 is structured to extend downwardly from the inner second surface 112i of the implant body 112. The window member 130 is fully transparent to provide an optical window through the dura 12. As such, and as discussed above, the window member 130 is composed of clear PMMA since it's fully translucent, radiolucent, sonolucent, and visually transparent. In addition, the window member 130 is constructed to have a soft, pliable form when manufactured in order to allow for proper dural pulsations and cerebral spinal fluid flow underneath.

The window member 130 is preferably constructed with a circular (or oval) configuration when viewed along a bottom elevation view and, therefore, includes an upper first surface 130u coextensive with the inner second surface 112i of the implant body 112, a lower second surface 130l opposite the upper first surface 130u, and a peripheral edge 130p extending between the upper first surface 130u and the lower second surface 130l. The peripheral edge 130p is shaped and dimensioned for positioning within an opening 12o (that is, a dural defect) formed within the dura 12 such that the window member 130, when properly installed, is flush with the dura 12. Such an opening 12o is contemplated to have a diameter of approximately 5 mm to 45 mm, preferably 35 mm to 45 mm, although it is well appreciated the size may be varied depending upon the reason the patient is being treated with the reconstructive cranial implant 110 so long as it sits beneath the implant body and provides for the desired visual and/or optical access. In accordance with an embodiment, the window member 130 has a thickness approximately the same as that of the dura 12 in the area in which the window member 130 is to be positioned. In accordance with another embodiment the window member 130 has a thickness similar to or less than the thickness of the cranial bone.

Installation of the window member 130 within the opening 12o formed in the dura 12 is facilitated by the provision of a coupling ring 132. The coupling ring 132 includes an inner circumference surface 132i shaped and dimensioned for coupling with the window member 130 and an outer circumference surface 132o shaped and dimensioned for engagement with the inner surface 112i of the opening 12o formed in the dura 12. As will be explained below in greater detail, this allows the coupling ring 132 to be first installed within the opening 12o formed in the dura 12 followed by the installation of the window member 130 within the space defined by the coupling ring 132. Installation of the window member 130 within the coupling ring 132 is facilitated by providing the inner circumferential surface 132i of the coupling ring 132 and the outer circumferential surface 132o of the window member 130 with mating coupling surfaces allowing for ready and secure attachment, for example, threaded coupling, bayonet coupling members, flanges, etc.

It is contemplated the coupling ring 132 may take a variety of forms and be secured within the opening 12o formed in the dura 12 via various mechanisms. For example, the coupling ring 132 may be a rigid ring that is held within the opening 12o formed in the dura 12 via zip ties, sutures, packing holes, elastic bands, screws (for example, Ti screws), and/or lock fixtures along the outer surface of the rigid ring. Regardless of the mechanism used to secure the coupling ring 132 within the opening 12o formed in the dura 12, it is contemplated that sealant 140 may be applied between the edge 12e of the opening 12o formed in the dura 12 and the outer circumferential surface 132o of the coupling ring 132. The sealant 140 is used to ensure a tight seal between the edge 12e of the opening 12o formed in the dura 12 and the outer circumferential surface 132o of the coupling ring 132, and the sealant 140 may be fibrin glue, dura sealant, or other sealant materials known within the industry.

In accordance with another embodiment, the coupling ring 132 may take the form of a shape memory ring (that is, made from Nitinol shape memory material) that expands upon application within the opening 12o formed in the dura 12. A shape memory ring such as this is constructed to expand to a predetermined diameter sufficient to create slight pressure between the edge 12e of the opening 12o formed in the dura 12 and the outer circumferential surface 132o of the shape memory ring. As with the embodiment discussed above, it is contemplated that sealant 140 may be applied between the edge 12e of the opening 12o formed in the dura 12 and the outer circumferential surface 132o of the coupling ring 132. The sealant 140 is used to ensure a watertight seal between the edge 12e of the opening 12o formed in the dura 12 and the outer circumferential surface 32o of the coupling ring 132, and the sealant 140 may be fibrin glue, dura sealant, or other sealant materials known within the industry.

In practice, and with the reconstructive cranial implant 110 fully fabricated and assembled, the skull 24 is resected so as to remove a preselected portion of the skull 24. With the resected portion of the skull 24 removed, an opening 12o is formed in the dura 12. Thereafter, the coupling ring 132 is positioned within the opening 12o formed in the dura 12 and is secured thereto using the mechanisms discussed above. The window member 130 is then positioned within the coupling ring 132 and secured thereto. The reconstructive cranial implant 110 is then secured to the skull using conventional techniques.

It should be appreciated that the positioning of the coupling ring 132 will likely create bunching and thickening of the dura 12 surrounding the coupling ring 132. As such, the thickness of the coupling ring 132 is designed so as to accommodate the increased thickness of the dura 12 in the vicinity of the coupling ring 132. Further still, the thickness of the window member 130 may be adjusted so as to accommodate space within the skull 24 as may be seen fit for specific applications.

Figures 4, 5:
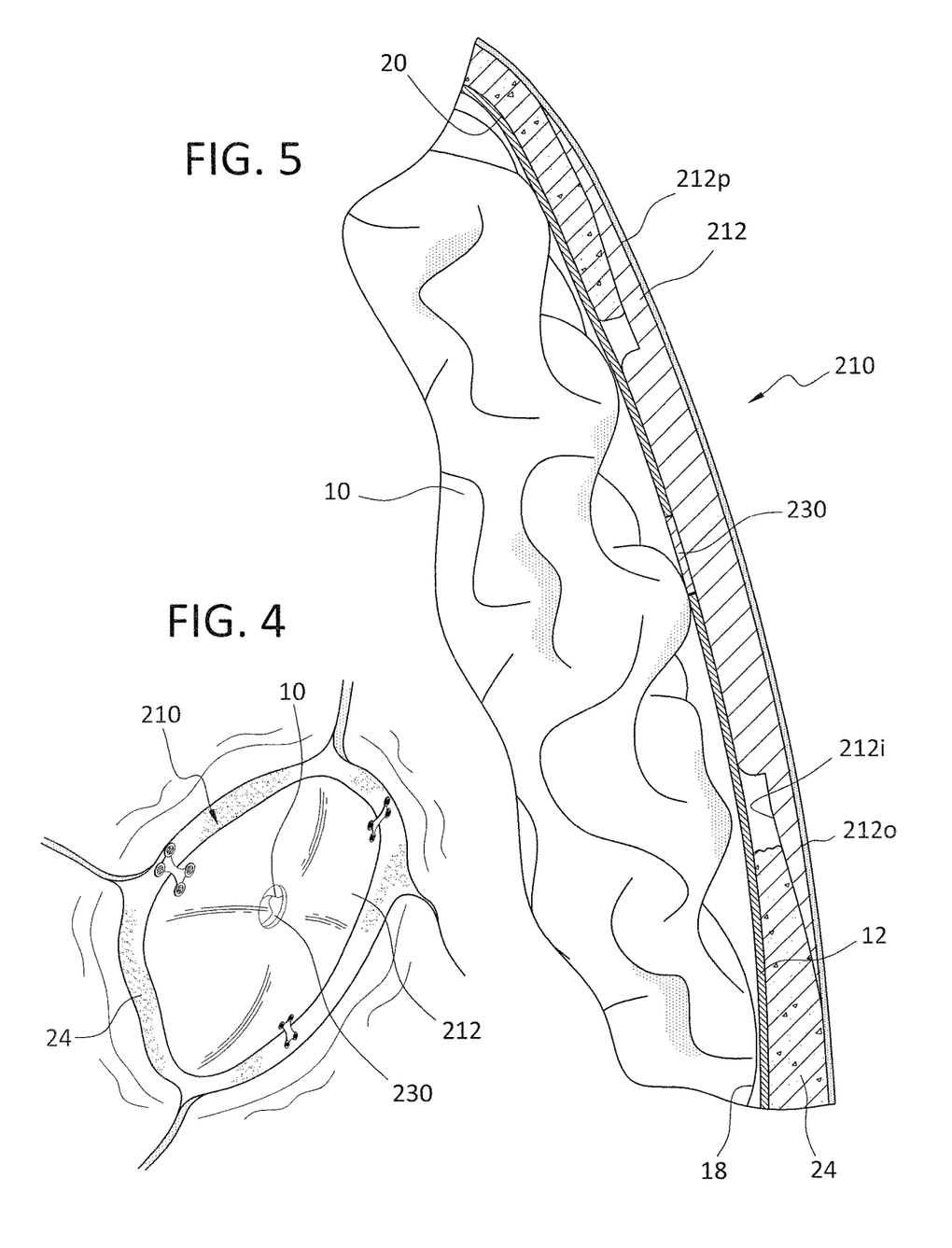
FIG. 4 is a perspective view of an installed cranial implant in accordance with a second embodiment.
FIG. 5 is a cross sectional view of the installed cranial implant shown in FIG. 4.
Figure 6:
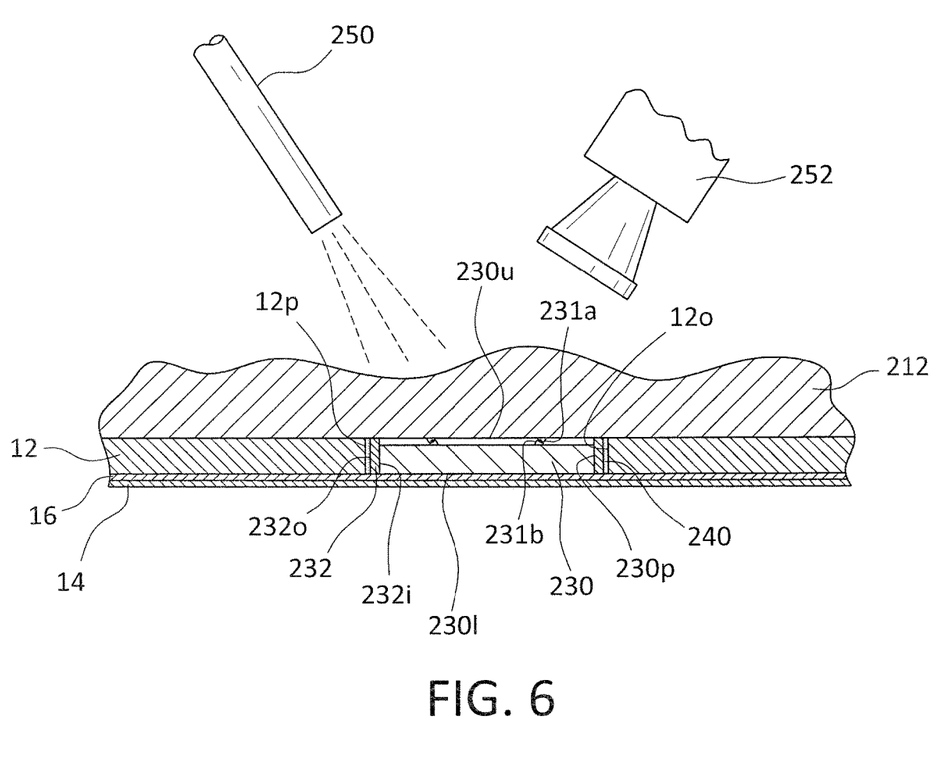
FIG. 6 is a detailed cross-sectional view of the installed cranial implant shown in FIG. 4. It should be appreciated the surfaces of the dural window member and the implant body are shown as being substantially flat although it is appreciated these surfaces may be contoured as dictated by specific anatomical features and optical characteristics of the cranial implant.

In accordance with the embodiment wherein the window member 230 is separate from the implant body 212 of the reconstructive cranial implant 210, and with reference to FIGS. 4 to 6, the window member 230 is constructed as a separate element that is selectively secured to the underside 212i of the implant body 212. The window member 230 is a disc-shaped member having a circular (oval) configuration when viewed along a top plan view and, therefore, includes an upper first surface 230u, a lower second surface 230l opposite the upper first surface 230u, and a peripheral edge 230p extending between the upper first surface 230u and the lower second surface 230l. The peripheral edge 230p is shaped and dimensioned for positioning within an opening 12o formed within the dura 12 such that the window member 230, when properly installed, is flush with the dura 12. Such an opening 12o is contemplated to have a diameter of approximately 5 mm to 45 mm, preferably 35 mm to 45 mm, although it is well appreciated the size may be varied depending upon the reason the patient is being treated with the reconstructive cranial implant 210 so long as it sits beneath the implant body and provides for the desired visual and/or optical access. In accordance with an embodiment, the window member 230 has a thickness approximately the same as that of the dura 12 in the area in which the window member 230 is to be positioned. In accordance with another embodiment the window member 230 has a thickness similar to or less than the thickness of the cranial bone. As with the prior embodiment, the window member 230 is constructed from clear PMMA or similar biomaterial and is constructed to have a soft, pliable form when manufactured in order to allow for proper dural pulsations and cerebral spinal fluid flow underneath.

As with the prior embodiment, installation of the window member 230 within the opening 12o formed in the dura 12 is facilitated by the provision of coupling ring 232. The coupling ring 232 includes an inner circumference surface 232i shaped and dimensioned for coupling with the window member 230 and an outer circumference surface 232o shaped and dimensioned for engagement with the inner surface 12i of the opening 12o formed in the dura 12. As will be explained below in greater detail, this allows the coupling ring 232 to be first installed within the opening 12o formed in the dura 12 followed by the installation of the window member 230 within the space defined by the coupling ring 232. Installation of the window member 230 within the coupling ring 232 is facilitated by providing the inner circumferential surface 232i of the coupling ring 232 and the outer circumferential surface 232o of the window member 230 with mating coupling surfaces allowing for ready and secure attachment, for example, threaded coupling, bayonet coupling members, flanges, etc.

It is contemplated the coupling ring 232 may take a variety of forms and be secured within the opening 12o formed in the dura 12 via various mechanisms. For example, the coupling ring 232 may be a rigid ring that is held within the opening 12o formed in the dura 12 via zip ties, sutures, packing holes, elastic bands, screws (for example, Ti screws), and/or lock fixtures along the outer surface of the rigid ring. Regardless of the mechanism used to secure the coupling ring 232 within the opening 12o formed in the dura 12, it is contemplated that sealant 240 may be applied between the edge 12p of the opening 12o formed in the dura 12 and the outer circumferential surface 232o of the coupling ring 232. The sealant 240 is used to ensure a watertight seal between the edge of the opening 12o formed in the dura 12 and the outer circumferential surface 232o of the coupling ring 232, and the sealant 240 may be fibrin glue, dura sealant, or other sealant materials known within the industry.

In accordance with another embodiment, the coupling ring 232 may take the form of a shape memory ring (that is, made from Nitinol shape memory material) that expands upon application within the opening 12o formed in the dura 12. A shape memory ring 230 such as this is constructed to expand to a predetermined diameter sufficient to create slight pressure between the edge 12e of the opening 12o formed in the dura 12 and the outer circumferential surface 232o of the shape memory ring 230. As with the embodiment discussed above, it is contemplated that sealant 240 may be applied between the edge 12p of the opening 12o formed in the dura 12 and the outer circumferential surface 232o of the coupling ring 232. The sealant 240 is used to ensure a watertight seal between the edge of the opening 12o formed in the dura 12 and the outer circumferential surface 232o of the coupling ring 232, and the sealant 240 may be fibrin glue, dura sealant, or other sealant materials known within the industry.

As briefly mentioned above, the window member 230 of this embodiment is shaped and dimensioned for selective engagement with the inner second surface 212i of the implant body 212 of the reconstructive cranial implant 210. The selective engagement may be achieved in a variety of ways within the spirit of the present invention. For example, the surfaces may be provided with mating hooks and/or latching structures 231a, 231b.

In practice, and with the low-profile intercranial device 210 fully fabricated and assembled, the normal-appearing skull 24 is resected so as to remove a preselected portion of the skull 24. This is a major difference and novel advancement since most cranial implants are designed for pre-existing skull defects and/or replacement of diseased skull, and not to incorporate dural attachment. With the resected portion of the skull 24 removed, an opening 12o is formed in the dura 12. Thereafter, the coupling ring 232 is positioned within the opening 12o formed in the dura 12 and is secured thereto using the mechanisms discussed above. The window member 230 is then positioned within the coupling ring 232 and secured thereto. The implant body 212 of reconstructive cranial implant 210 is then secured to the window member 230 and the reconstructive cranial implant 210 is subsequently secured to the skull 24 using known techniques.

It should be appreciated that the positioning of the coupling ring 232 will likely create bunching and thickening of the dura 12 surrounding the coupling ring 232. As such, the thickness of the coupling ring 232 is designed so as to accommodate the increased thickness of the dura 12 in the vicinity of the coupling ring 232. Further still, the thickness of the window member 230 may be adjusted so as to accommodate space within the skull 24 as may be seen fit for specific applications.

It is appreciated that some patients will not require skull reconstruction and the cranial implant might not be necessary. As such, it is contemplated the window member could be utilized by itself with the resected portion of the skull simply positioned over the window member. In accordance with such a variation, the installation of the window member would be similar to the procedure described above, and this could solely provide a pliable, soft, window member extension.

With the embodiments of FIGS. 1 to 3 and 4 to 6 in mind, it is appreciated the clear reconstructive cranial implant 110, 210 composed of an implant body 112, 212 and a clear dural window member 130, 230 may be used in conjunction with a variety of externally positioned diagnostic devices. For example, and as shown with reference to FIGS. 3 and 6, it is contemplated the clear reconstructive cranial implant 110, 210 and a clear dural window member 130, 230 may be used with various light sources 150, 250, video recording mechanisms 152, 252, and other devices requiring direct visualization of the brain cortex.

With reference to FIGS. 7 to 12, two embodiments of a cranial implant in the form of a low-profile intercranial device 410, 510 (as disclosed in Applicant's earlier patent applications) incorporating a window member 430, 530 are disclosed. That is, the low-profile intercranial devices described in Applicant's own U.S. Patent Application Publication No. 2018/0055640, entitled "METHOD FOR MANUFACTURING A LOW-PROFILE INTERCRANIAL DEVICE AND THE LOW-PROFILE INTERCRANIAL DEVICE MANUFACTURED THEREBY," filed Aug. 4, 2017, and PCT Publication No. WO 2017/039762, entitled "LOW-PROFILE INTERCRANIAL DEVICE," filed May 2, 2016, which are incorporated herein by reference, may be implemented with the window member 430 integrally formed with a cranial implant (as disclosed above with reference to FIGS. 7 to 9) or with the window member 530 formed as a separate unit that is selectively secured to a cranial implant (as disclosed above with reference to FIGS. 10 to 12). Regardless of the embodiment employed, the window member 430, 530 provides a clear view through the dura 12 such that visual access to the cerebral cortex 18 is fully provided in the location under study. If the window member is flexible enough, it may be used for dural replacement as well.

As with the prior embodiments, it is appreciated that the following disclosure relates to a low-profile intercranial device 410, 510 adapted for adult patients. As such, and considering the fact the dura 12 is much thinner in pediatric neurosurgery patients and/or irradiated patients, the low-profile intercranial device 410, 510 may be slightly modified to suit these anatomical variables.

In accordance with the embodiment of FIGS. 7 to 12, the low-profile intercranial device 410, 510 includes a low-profile customized intercranial implant body 412, 512 and a functional neurosurgical implant 414, 514 meshed together to ultimately define a single product. It is appreciated that while the various embodiments disclosed herein only show a single functional neurosurgical implant 414, 514 in conjunction with a low-profile customized cranial implant 412, 512, multiple functional neurosurgical implants 414, 514 (or no functional neurosurgical implants) may be used in a low-profile intercranial device 410, 510.

The low-profile customized intercranial implant body 412, 512 of the disclosed embodiment is a modified version of a low-profile cranial implant commonly used and known by those skilled in the art of cranial surgical and neuroplastic procedures. Such implants may take a variety of forms and are most commonly shaped and dimensioned for integration into the structure of a patient's skull; that is, the low-profile customized intercranial implant body 412, 512 has a geometry that substantially conforms to a resected portion of the patient's anatomy to which the implant is to be secured. Briefly, the low-profile customized intercranial implant body 412, 512 includes an outer (commonly convex) first surface 412o, 512o, an inner (commonly concave) second surface 412i, 512i, and a peripheral edge 412p, 512p extending between the outer first surface 412o, 512o and the inner second surface 412i, 512i. The low-profile customized intercranial implant body 412, 512 is shaped and dimensioned for engagement with the skull of the patient upon implantation in a manner well known to those skilled in the field of neurosurgical procedures. The outer first surface 412o, 512o and inner second surface 412i, 512i of the low-profile customized intercranial implant body 412, 512 are preferably curved in a superior to inferior direction, a posterior to anterior direction, and a medial to lateral direction. In addition, the peripheral edge 412p, 512p has a substantial taper for resting upon a matching taper formed along the skull. It is, however, appreciated that this taper may vary (or not exist at all, that is, the peripheral edge 412p, 512p may be substantially perpendicular relative to the outer first surface 412o, 512o and the inner second surface 412i, 512i) depending upon the specific needs of the procedure.

In accordance with these embodiments, the low-profile customized intercranial implant body 412, 512 has a preselected thickness not exceeding the space between the inner surface of the scalp and the outer surface of the dura, for example, in the range of around 1 millimeter to 25 millimeters (with areas of strategic bulking and/or thinning) and depending upon the strength of the materials used in the construction of the low-profile customized intercranial implant body 412, 512. Preferably, the low-profile customized intercranial implant body 412, 512 will have a thickness of 1 millimeter to 12 millimeters. Furthermore, if there is a brain cavity present underneath from a previous brain seizure focus resection and/or brain tumor, additional bulking of the implant would be advantageous to minimize deadspace underneath; thereby, minimizing risks of fluid collection and/or super infection.

Because the low-profile customized intercranial implant body 412, 512 of the disclosed embodiments is intended to house a functional neurosurgical implant 414, 514, the low-profile customized intercranial implant body 412, 512 also includes a cavity 416, 516 (for example, formed along the inner surface) and optional structural elements 418, 518, for example, channels, pockets, access holes, and/or other structural elements, designed to accommodate various features of the functional neurosurgical implant 414, 514. In the disclosed embodiment, structural elements 418, 518 in the form of channels are provided. The channels 418, 518 have a first end 418a, 518a in communication with the cavity 416, 516 and a second end 418b, 518b extending to the inner second surface (or bottom surface) 412i, 512i of the low-profile customized intercranial implant body 412, 512 for the passage of electrodes of the functional neurosurgical implant 414, 514 for applying stimulation to the brain.

In accordance with an embodiment, and as with the embodiments disclosed above with reference to FIGS. 1 to 6, the low-profile customized intercranial implant body 412, 512 is fabricated from a wide array of commonly-available biomaterials, but, and in accordance with an embodiment, the low-profile customized intercranial implant body 412, 512 is ideally made of clear PMMA or similar material since it's fully translucent to light, sonolucent to ultrasound (as first described by Gordon et al. in "Sonolucent Cranial Implants: Cadaveric Study and Clinical Findings Supporting Diagnostic and Therapeutic Trans-Cranioplasty Ultrasound." J Craniofac Surg 2019 and Gordon et al. in "Trans-Cranioplasty Ultrasound (TCU) through a Sonolucent Cranial Implant Made of Poly-methyl methacrylate (PMMA): Phantom Study Comparing Ultrasound, CT and MRI." J Craniofac Surg 2019), permeable to low-coherence light used in optical coherence tomography (OCT), radiolucent, for example, to ECoG signals, and transparent for ideal visualization necessary for brain lead placement, catheter positioning, etc. This allows for inspection of the interdigitated functional neurosurgical implant 414, 514, the brain, and neighboring components. As will be explained below in greater detail, it also allows for the critical transmission of vital imaging with minimal distortion, such as ultrasound waves for brain pathology detection, low-coherence light used in optical coherence tomography (OCT), and wireless signal communication (i.e., electroencephalography or ECoG)—essential for various neuromodulation devices such as NeuroPace®, for example. In summary, the utilization of an optically lucent, sonolucent, and radiolucent material provides for photoacoustic mapping, remote stimulation, ablation, and imaging of neurophysiology, as well as dilation of the blood brain barrier. Another clear material that may be readily used in accordance with the present cranial implant is cubic zirconium or plastic.

The optical clarity of the low-profile customized intercranial implant body 412, 512 is important in implementing the uses of the low-profile intercranial device 410, 510 and in expanding the potential functional neurosurgical implants 414, 514 that may be used in conjunction therewith. For example, the provision of high optical clarity allows for wireless optical links between the functional neurosurgical implants 414, 514 and remote devices or between functional neurosurgical devices on the interior of the cranium and the exterior of the low-profile intercranial device 410, 510 (for example, transmitting between the cortex and the other side of the low-profile intercranial device). Enhanced optical clarity similarly allows for power transmission and/or receipt between the functional neurosurgical implants 414, 514 and devices outside of the low-profile customized intercranial implant body 412, 512. Potential operations that may be achieved through the utilization of optical links through a high clarity low-profile customized intercranial implant body 412, 512 include, but are not limited to, device start-up, device calibration, device operational control, data management, and remote alerting of physicians/surgeons with abnormal findings (similar to remote monitoring via cardiac pacemakers/defibrillators).

Still further, the low-profile customized intercranial implant body 412, 512 is constructed from a material allowing for imaging of the brain through the low-profile customized intercranial implant body 412, 512, for example, via ultra-sound or optical coherence tomography. It is known that clear PMMA will provide the ability to permit ultrasound imaging and low-coherence light used in optical coherence tomography (OCT) imaging of the brain therethrough so long as it is manufactured without additives that might function to block the radio waves of the imaging device.

The functional neurosurgical implant 414, 514 is selected from a variety of FDA-approved and experimental options for electrical, optical, mechanical, medicinal, and other treatment/monitoring devices designed for long term invasive treatment and/or disease-monitoring of patients requiring such attention. These functional neurosurgical implants 414, 514 are known devices manufactured by various vendors within the neurosurgical industry and have known, unmodifiable dimensions that may be used in conjunction with the low-profile customized intercranial implant body 412, 512 to optimize surgical results by minimizing abnormal shapes, visible contours, and/or craniofacial deformities. With this in mind, the term "functional neurosurgical implant" is meant to reference any therapeutic hardware or compositions including, but not limited to, medicines to treat any patient-specific illness, or electronic, mechanical, imaging modality and/or electro-mechanical device to remotely monitor (e.g., via. Wi-Fi connectivity) or intervene in any specific neurologic illness, including imaging, monitoring, electrostimulation, radiation therapy, or polarized light/laser neuronal modulation devices. Of particular note, functional neurosurgical implants 414, 514 requiring light waves that might otherwise be blocked by the dura are especially suited for use in conjunction herewith. For example, functional neurosurgical implants 414, 514 providing for optical coherence tomography (OCT) imaging, video imaging, and transcranial infrared therapy would be especially well suited for use herewith.

Figures 7, 8:
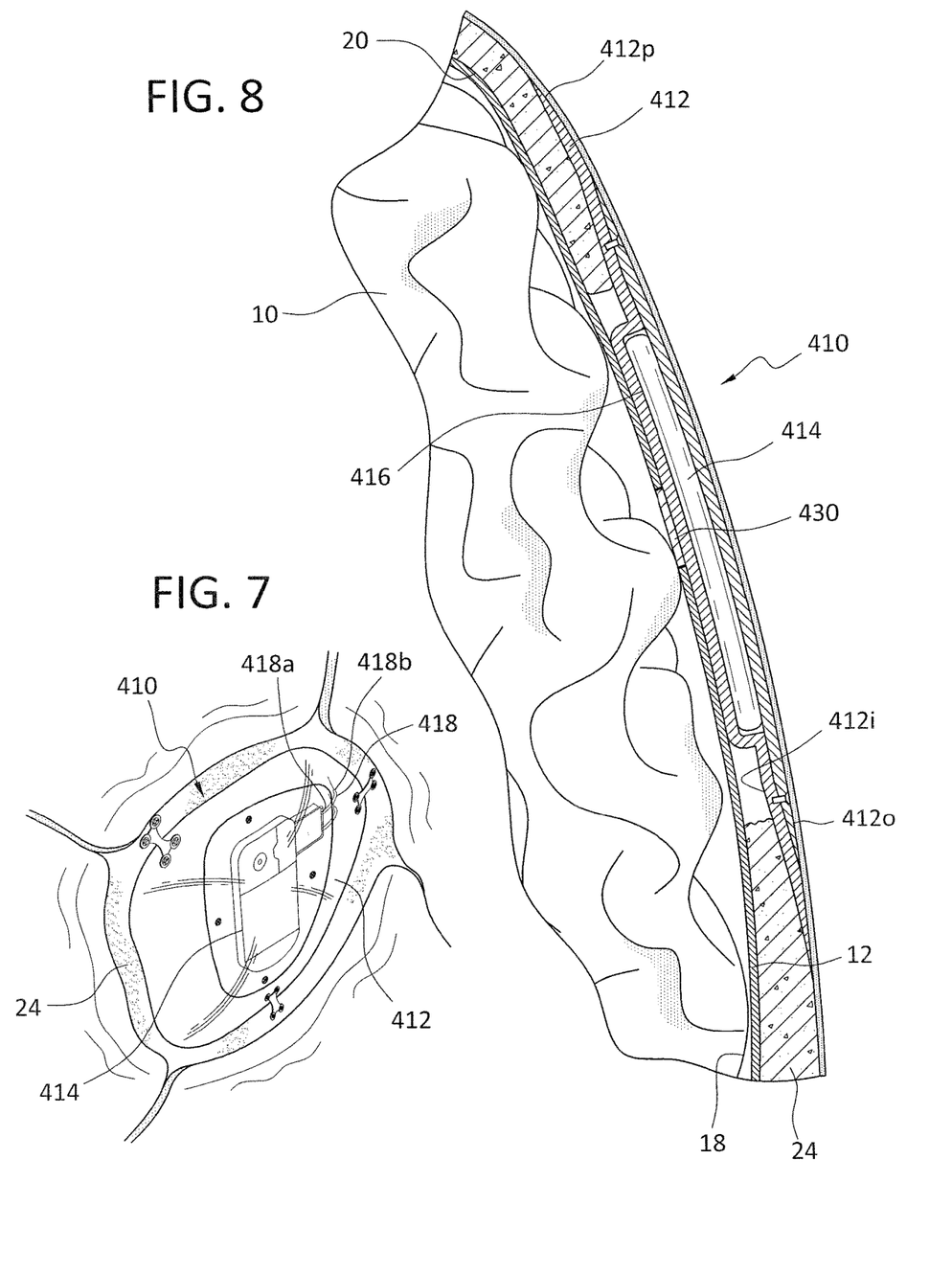
FIG. 7 is a perspective view of an installed low-profile intercranial device in accordance with yet another embodiment.
FIG. 8 is a cross sectional view of the installed low-profile intercranial device shown in FIG. 7.
Figure 9:
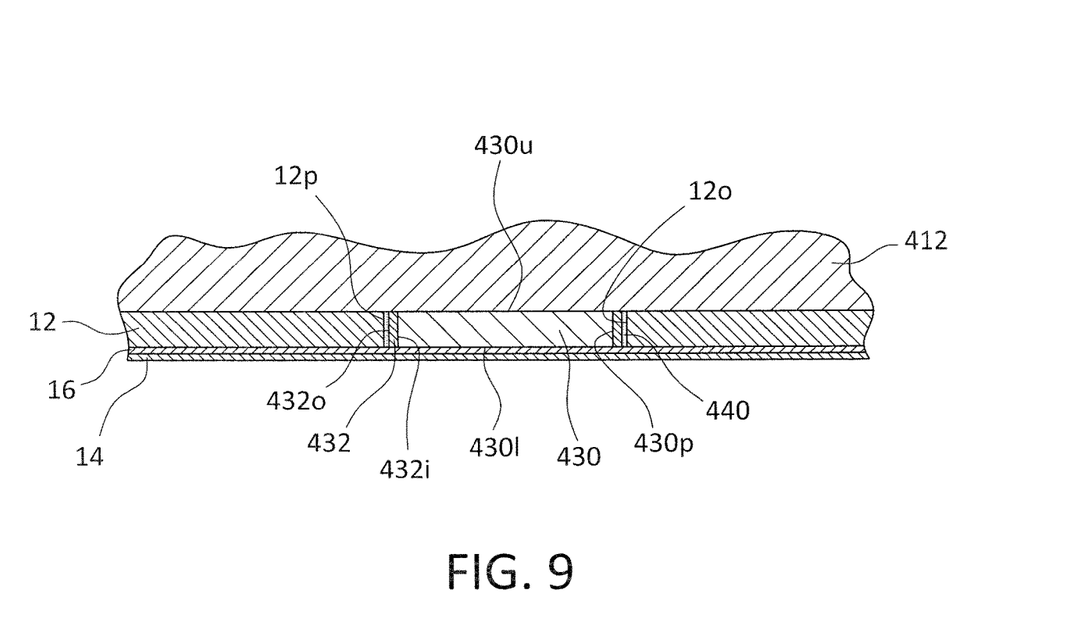
FIG. 9 is a detailed cross-sectional view of the installed low-profile intercranial device shown in FIG. 7. It should be appreciated the surfaces of the dural window member and the low-profile customized intercranial implant body are shown as being substantially flat although it is appreciated these surfaces may be contoured as dictated by specific anatomical features and optical characteristics of the low-profile intercranial device.

In accordance with the embodiment disclosed with reference to FIGS. 7 to 9, the window member 430 is formed as an integral part of the low-profile intercranial device 410, and the window member 430 is structured to extend downwardly from the inner second surface 412*i* of the low-profile customized intercranial implant body 412. The window member 430 is fully transparent to provide an optical window through the dura 12. As such, the window member 430 is composed of clear PMMA since it's fully translucent, radiolucent, sonolucent and visually transparent. In addition, the window member 430 is constructed to have a soft, pliable form when manufactured in order to allow for proper dural pulsations and cerebral spinal fluid flow underneath. The window member 430 is preferably constructed with a circular (or oval) configuration as described above with reference to FIGS. 1 to 3. Installation of the window member 430 within the opening 12*o* formed in the dura 12 is facilitated by the provision of a coupling ring 432 as described above with reference to FIGS. 1 to 3.

In practice, and with the low-profile intercranial device 410 fully fabricated and assembled, the skull 24 is resected so as to remove a preselected portion of the skull 24. With the resected portion of the skull 24 removed, an opening 12*o* is formed in the dura 12. Thereafter, the coupling ring 432 is positioned within the opening 12*o* formed in the dura 12 and is secured thereto using the mechanisms discussed above. The window member 430 is then positioned within the coupling ring 432 and secured thereto. The low-profile customized intercranial implant body 412 is then secured to the skull using conventional techniques.

Figures 10, 11:
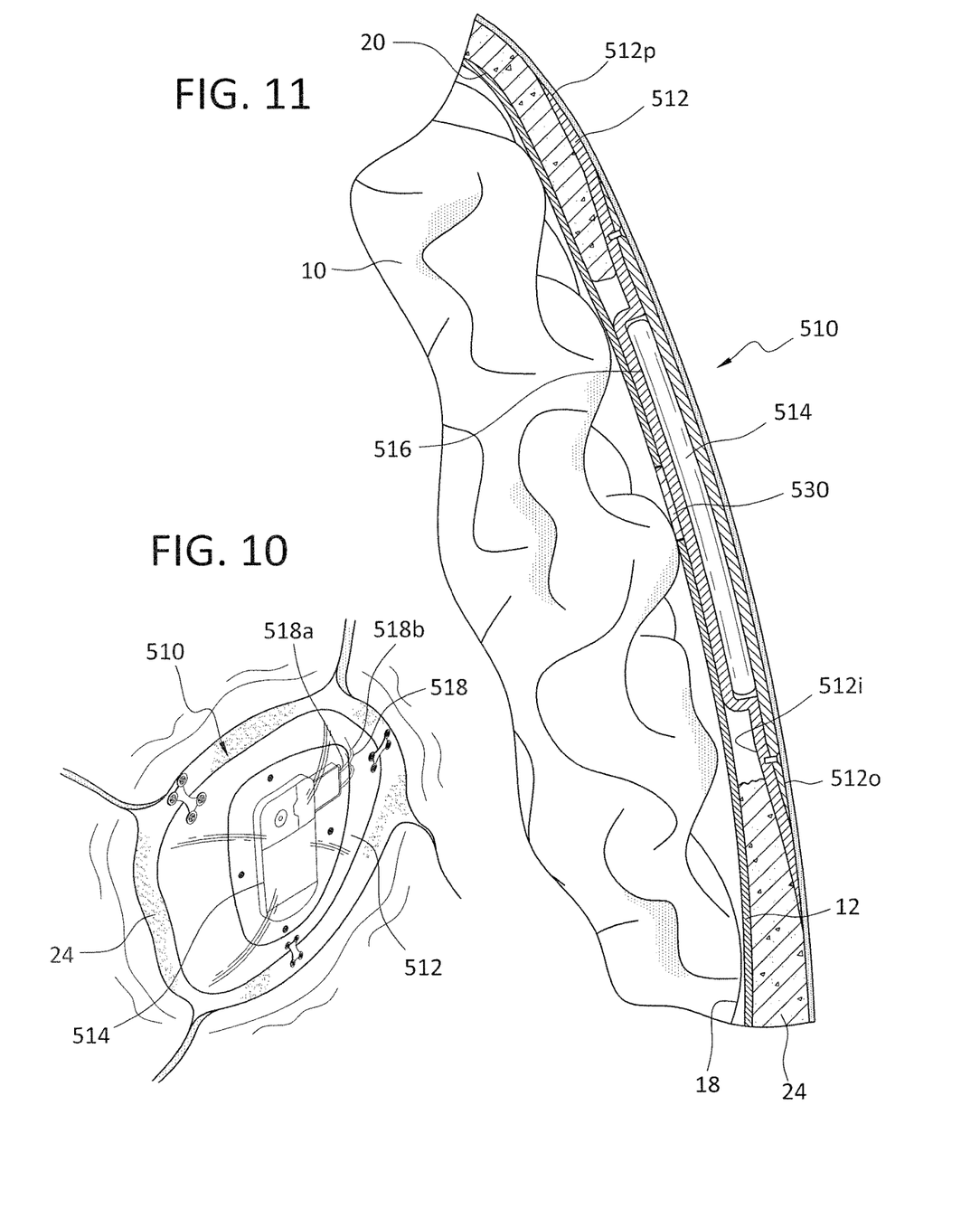
FIG. 10 is a perspective view of an installed low-profile intercranial device in accordance with yet another embodiment.
FIG. 11 is a cross sectional view of the installed low-profile intercranial device shown in FIG. 10.
Figure 12:
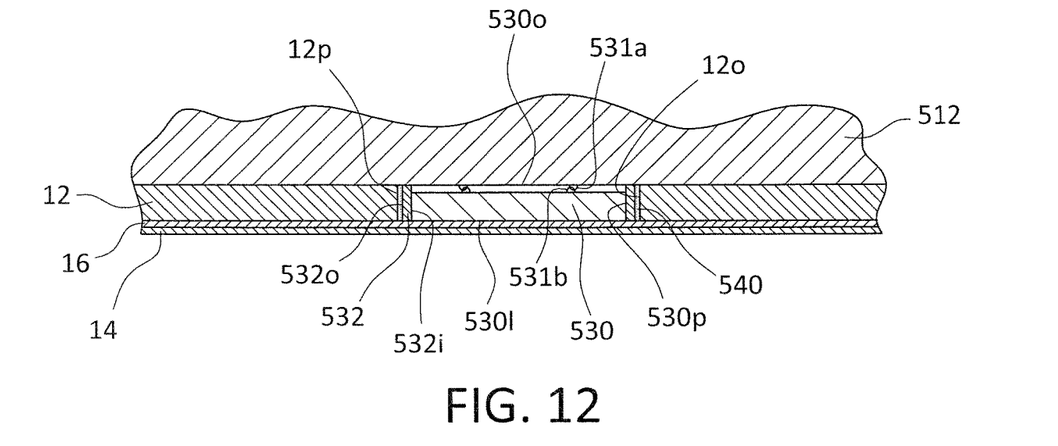
FIG. 12 is a detailed cross-sectional view of the installed low-profile intercranial device shown in FIG. 10. It should be appreciated the surfaces of the dural window member and the low-profile customized intercranial implant body are shown as being substantially flat although it is appreciated these surfaces may be contoured as dictated by specific anatomical features and optical characteristics of the low-profile intercranial device.

In accordance with the embodiment wherein the window member 530 is separate from the low-profile customized intercranial implant body 512, and with reference to FIGS. 10 to 12, the window member 530 is constructed as a separate element that is selectively secured to the underside 512*i* of the low-profile customized intercranial implant body 512. The window member 530 is structured as disclosed above with reference to FIGS. 4 to 6. As with the prior embodiment, installation of the window member 530 within the opening 12*o* formed in the dura 12 is facilitated by the provision of coupling ring 532. The coupling ring 532 is structured as described above with reference to FIGS. 4 to 6.

In practice, and with the low-profile intercranial device 510 fully fabricated and assembled, the normal-appearing skull 24 is resected so as to remove a preselected portion of the skull 24. This is a major difference and novel advancement since most cranial implants are designed for pre-existing skull defects and/or replacement of diseased skull, and not to include some form of dural attachment. With the resected portion of the skull 24 removed, an opening 12*o* is formed in the dura 12. Thereafter, the coupling ring 532 is positioned within the opening 12*o* formed in the dura 12 and is secured thereto using the mechanisms discussed above. The window member 530 is then positioned within the coupling ring 532 and secured thereto. The low-profile customized intercranial implant body 512 is then secured to the window member 530 and the low-profile customized intercranial implant body 512 is subsequently secured to the skull 24 using known techniques. As with the embodiment disclosed above with reference to FIGS. 4 to 6, the window member 530 of this embodiment is shaped and dimensioned for selective engagement with the inner second surface 512*i* of the implant body 512. The selective engagement may be achieved in a variety of ways within the spirit of the present invention. For example, the surfaces may be provided with mating hooks and/or latching structures 531*a*, 531*b*.

In accordance with an alternate embodiment, it is contemplated the window member and the implant body (in the case of the embodiments disclosed with reference to FIGS. 1-6) or low-profile customized intercranial implant body (in the case of the embodiments disclosed with reference to FIGS. 7-12) may be provided with etchings. As will be appreciated based upon the following disclosure, the etchings can be used to assist in alignment of the window member and implant body or low-profile customized intercranial implant body during the implantation process. The etchings can be used to assist in alignment of the window member and implant body/low-profile customized intercranial implant body with the brain structure (or other structural element upon the surface of the brain) during the implantation process. Finally, the etchings may also be used after implantation to monitor any shift that may occur between the window member, the implant body and/or the underlying brain structure (or other structural element upon the surface of the brain).

In describing this embodiment, the cranial implant of the embodiment disclosed with reference to FIGS. 4, 5 and 6 is generally shown (without the mating hooks and/or latching structures), that is, a two-piece assembly wherein the implant body and the window member are separate elements. They may or may not be fabricated from the same material, depending on the desired manufacturing process. However, the application of etchings as described herein may be utilized in conjunction with any of the embodiments described above. In accordance with one embodiment as shown with reference to FIG. 13, an outer first implant body etching 762 and an inner second implant body etching 764 are formed along the outer and inner surfaces 712*o*, 712*i*, respectively, of the implant body 712. A window etching 760 is formed on the window member 730. The window etching 760 and the implant body etchings 762, 764 are shaped and dimensioned such that when they are implanted and properly aligned one looking through the implant body 712 (or the low-profile customized intercranial implant body as disclosed with reference to the embodiments of FIGS. 7-12) and the window member 730 at the proper orientation will see the window etching 760 and the implant body etchings 762, 764 merge into a single location identifying image (for example, crosshairs or circles) 766 with a specific brain anatomy (or other structural element upon the surface of the brain) 26 identified by the single location identifying image 766. When the specific brain anatomy 26 identified by the single location identifying image 766 changes over time, the surgeon will know that something has shifted and will take appropriate action.

Figure 13:
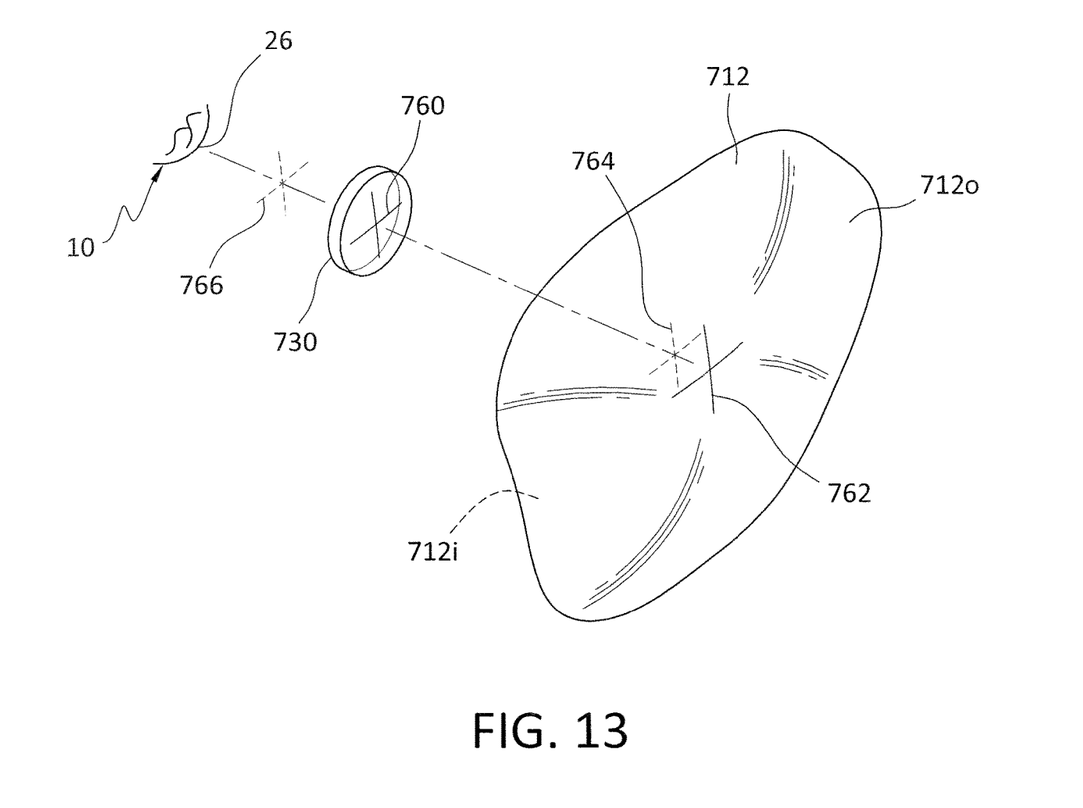
FIGS. 13, 14, and 15 are exploded perspective views showing various embodiments integrating etchings into the cranial implant.

Further, the outer first implant body etching 762 and inner second implant body etching 764 is shaped and positioned to assist in alignment of the cranial implant body 712 relative to the underlying window member 730 and brain anatomy during the implantation process. As briefly mentioned above, the window member 730 is provided with the window etching 760 for alignment with the first and second implant body etchings 762, 764 on the cranial implant body 712. These etchings 760, 762, 764 are useful during the implantation process because when the window etching 760 aligns with the upper first implant body etching 762 and the lower second implant body etching 764, proper alignment of the window member 730 and the implant body 712 is verified. These etchings 760, 762, 764 are also used after implantation to monitor any shift that may occur between the cranial implant body 712 and the window member 730. Similarly, the etchings 760, 762, 764 may be used to verify proper alignment with a specific brain anatomy (or other structural element upon the surface of the brain) during the implantation process.

It is contemplated only the cranial implant body may be marked with etchings. In accordance with such a variation, the upper first cranial implant body etching and lower second cranial implant body etching are formed such that when one is looking through the cranial implant body at a proper orientation, they will see the upper first cranial implant body etching and lower second etching merge into a single location identifying image (for example, crosshairs or circles) with a specific brain anatomy or a location on the dural window member identified by the single location identifying image.

Figure 14:
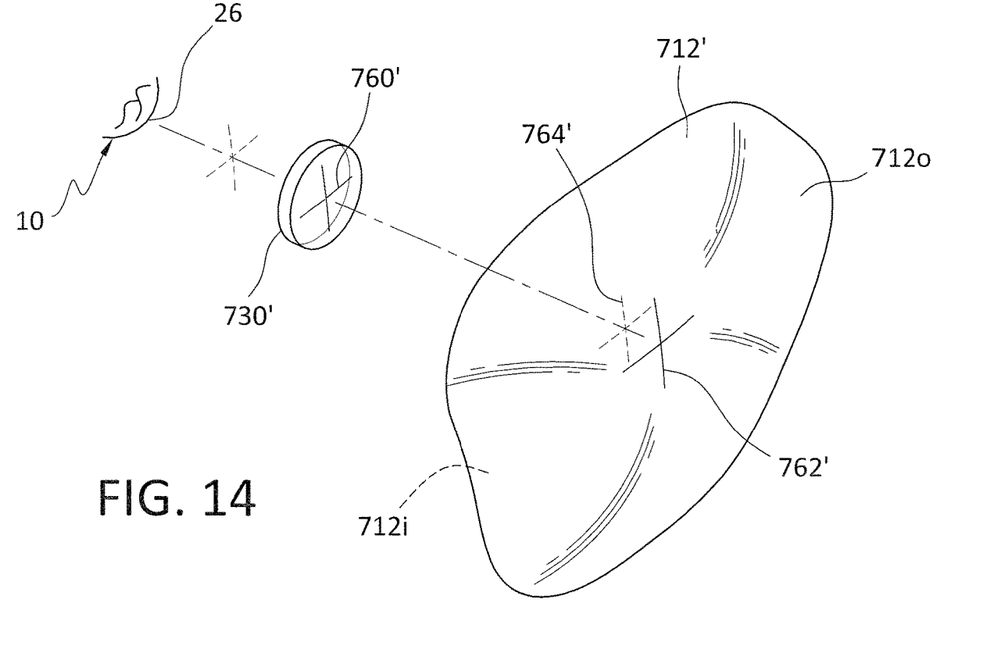

Further still, and with reference to FIG. 14, the window etching 760' and the cranial implant body etchings 762', 764' are not limited to simply optically visible etching, but may be made with radiographic materials allowing observation of the positioning of the window member 730' and the cranial implant body 712' via various image techniques. The information provided by the radiographically doped etchings of the window member 730' and the implant body 712' may be used by various computer-assisted/robotic-assisted surgical systems, navigation systems, and associated procedures, for example, as disclosed in U.S. Patent Application Publication Nos. 2017/0000564, entitled "COMPUTER-ASSISTED PLANNING AND EXECUTION SYSTEM," 2017/0000505, entitled "COMPUTER-ASSISTED CRANIOMAXILLOFACIAL SURGERY," 2017/0000566, entitled "COMPUTER-ASSISTED FACE-JAW-TEETH TRANSPLANTATION," 2017/0000498, entitled "PATIENT-SPECIFIC TRACKABLE CUTTING GUIDES," 2017/0000497, entitled "CRANIAL REFERENCE MOUNT," and 2017/0273797, entitled "COMPUTER ASSISTED CRANIOPLASTY," all of which are incorporated herein by reference in their entireties.

Figure 15:
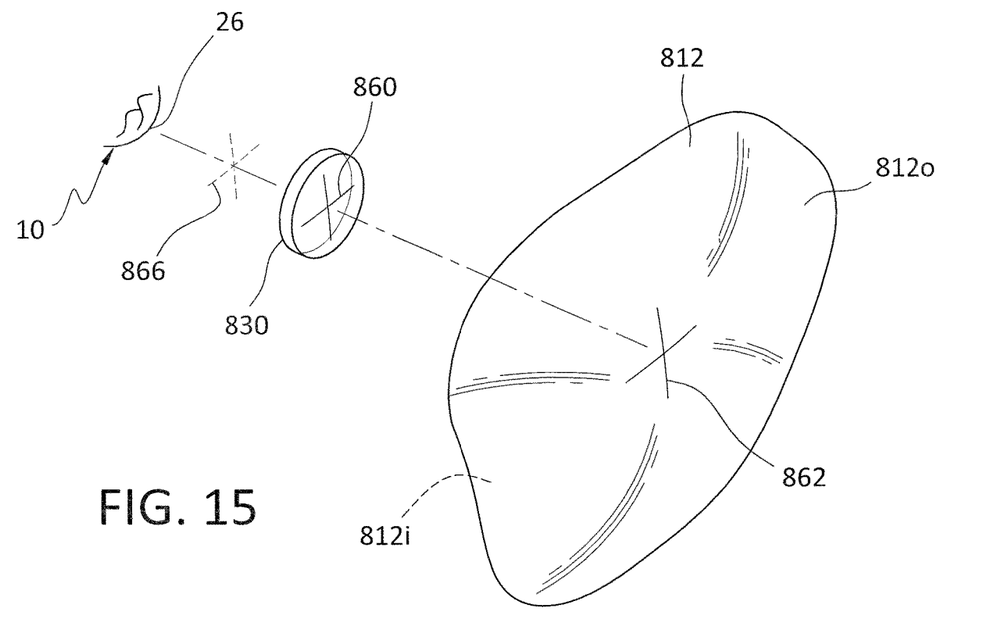

Further still, and with reference to FIG. 15, it is contemplated an implant body with a single implant body etching may be combined with a window member having a window etching. In accordance with such an embodiment, a first implant body etching 862 is formed along the outer or inner surface 812o, 812i of the implant body 812 and the window etching 860 is formed on the window member 830. The window etching 860 and the implant body etching 862 are shaped and dimensioned such that when they are implanted and properly aligned one looking through the implant body 812 (or the low-profile customized intercranial implant body as disclosed with reference to the embodiments of FIGS. 7-12) and the window member 830 at the proper orientation will see the window etching 860 and the implant body etching 862 merge into a single location identifying image (for example, crosshairs or circles) 866 with a specific brain anatomy (or other structural element upon the surface of the brain) 26 identified by the single location identifying image 866. When the specific brain anatomy 26 identified by the single location identifying image 866 changes over time, the surgeon will know that something has shifted and will take appropriate action. These etchings 860, 862 may also be used during implantation to verify proper alignment with a specific brain anatomy (or other structural element upon the surface of the brain) during the implantation process.

As with the prior embodiment, it is contemplated the etchings may be made with radiographic materials allowing observation of the positioning of the craniofacial implant via various image techniques. The information provided by the radiographically doped upper etchings may be used by various computer-assisted/robotic-assisted surgical systems, navigation systems, and associated procedures as disclosed above.

It is appreciated that some patients will not require skull reconstruction and the cranial implant might not be necessary. As such, it is contemplated the window member could be utilized by itself with the resected portion of the skull simply positioned over the window member. In accordance with such a variation, the installation of the window member would be similar to the procedure described above, and this could solely provide a pliable, soft, window member extension.

While the invention has been shown and described, it will be understood that there is no intent to limit the invention by such disclosure, but rather, is intended to cover all modifications and alternate constructions falling within the spirit and scope of the invention.

The invention claimed is:

1. A cranial implant for providing visual, optical, ultrasonic, or radiofrequency access to a cerebral cortex of a patient, the cranial implant comprising:
   a window member shaped and dimensioned for positioning within a dural defect defined by an opening formed within dura mater of a patient to provide access to the cerebral cortex, the window member being radiolucent, sonolucent, or visually transparent, the window member further including an upper first surface, a lower second surface opposite the upper first surface, and a peripheral edge extending between the upper first surface and the lower second surface; and
   an intercranial implant body shaped and dimensioned for integration into the patient's skull such that it has a geometry that is capable of conforming to a resected portion of the patient's anatomy to which the implant body is to be secured,
   wherein the intercranial implant body is radiolucent, sonolucent, or visually transparent, and
   wherein the intercranial implant body includes an upper first surface, a lower second surface opposite the upper first surface which is engaged with the upper first surface of the window member, and a peripheral edge extending between the upper first surface and the lower second surface, wherein the lower second surface is engaged with the upper first surface of the window member, such that the window member in positioned under the intercranial implant body;
   wherein the intercranial implant body includes at least one implant body etching and the window member includes a window etching, wherein when viewed from a specific location, the window etching and at least one implant body etching merge into a single, location-identifying image on a brain of the patient.

2. The cranial implant according to claim 1, wherein the at least one implant body etching and the window etching include radiographic materials.

3. The cranial implant according to claim 1, wherein the at least one implant body etching includes a first outer implant body etching and a second outer implant body etching respectively formed along outer and inner surfaces of the implant body.

4. The cranial implant according to claim 1, wherein the intercranial implant body is made of clear Poly(methyl methacrylate)(PMMA).

5. The cranial implant according to claim 1, further including a coupling ring securing the window member within the opening formed within the dura mater of the patient.

6. The cranial implant according to claim 5, wherein the coupling ring is made of a shape memory material.

7. The cranial implant according to claim 1, wherein the window member and the intercranial implant body are separate and distinct elements.

8. The cranial implant according to claim 7, wherein mating hooks and/or latching structures secure the window member to the intercranial implant body.

9. The cranial implant according to claim 1, wherein the window member is sonolucent allowing for passage of ultrasonic waves therethrough.

10. The cranial implant according to claim 1, wherein the window member is optically clear in the visible light spectrum allowing for optical and/or visual access therethrough.

\* \* \* \* \*